United States Patent
Wright et al.

(10) Patent No.: US 9,737,238 B2
(45) Date of Patent: Aug. 22, 2017

(54) METHODS FOR DETERMINING THE SIZE OF BODY PARTS AS PART OF COMPRESSION THERAPY PROCEDURES

(71) Applicant: Wright Therapy Products, Inc., Oakdale, PA (US)

(72) Inventors: Carol L. Wright, Pittsburgh, PA (US); Gregory Yurko, Murrysville, PA (US)

(73) Assignee: Wright Therapy Products, Inc., Oakdale, PA (US)

( * ) Notice: Subject to any disclaimer, the term of this patent is extended or adjusted under 35 U.S.C. 154(b) by 63 days.

(21) Appl. No.: 13/966,741

(22) Filed: Aug. 14, 2013

(65) Prior Publication Data

US 2014/0052028 A1 Feb. 20, 2014

Related U.S. Application Data

(60) Provisional application No. 61/684,720, filed on Aug. 18, 2012.

(51) Int. Cl.
*A61B 5/103* (2006.01)
*A61B 5/117* (2016.01)
(Continued)

(52) U.S. Cl.
CPC .......... *A61B 5/1073* (2013.01); *A61B 5/1072* (2013.01); *A61B 5/1074* (2013.01);
(Continued)

(58) Field of Classification Search
CPC .............. A61H 9/0078; A61H 2209/00; A61F 2002/7615; A61F 2002/762;
(Continued)

(56) References Cited

U.S. PATENT DOCUMENTS 3,811,431 A 5/1974 Apstein
4,011,860 A 3/1977 Lee
(Continued)

FOREIGN PATENT DOCUMENTS

DE 19846922 A1 4/2000
FR 2682279 A1 4/1993
(Continued)

OTHER PUBLICATIONS

Motorola, Integrated silicone Pressure Sensor On-Chip Signal Conditioned, Temperature Compensated and Calibrated; MPX5050 MPXV5050G Series, 2002.

*Primary Examiner* — Devin Henson
(74) *Attorney, Agent, or Firm* — Shumaker, Loop & Kendrick, LLP (57) ABSTRACT

Methods are disclosed for measuring the size of body parts treated by a compression therapy device. Either the volume or circumference of the body part may be measured. The methods may include evacuating an inflatable compression sleeve to a known pressure, inserting the body part into the compression sleeve, inflating the sleeve to a pre-set condition, and then measuring one or more inflation related parameters. The pre-set conditions may include a pre-determined pressure, volume, or size of the inflatable cells comprising the sleeve. The inflation related parameters may include the time to fill the cell to a pre-set pressure, the pressure attained after a pre-set time of inflation, or the measured volume of a cell after a pre-set amount of air is introduced into it. The methods may also include deflating the cells from the known inflation state to a second inflation state and measuring similar parameters.

17 Claims, 5 Drawing Sheets

(51) Int. Cl.
*A61B 5/107* (2006.01)
*A61B 5/00* (2006.01)
*A61H 9/00* (2006.01)
*A61F 2/76* (2006.01)

(52) U.S. Cl.
CPC .......... *A61B 5/1075* (2013.01); *A61B 5/6812* (2013.01); *A61B 5/6824* (2013.01); *A61B 5/6828* (2013.01); *A61B 5/7246* (2013.01); *A61B 5/7278* (2013.01); *A61B 5/0053* (2013.01); *A61B 5/4836* (2013.01); *A61B 5/4878* (2013.01); *A61F 2002/762* (2013.01); *A61F 2002/7615* (2013.01); *A61H 9/0078* (2013.01); *A61H 9/0092* (2013.01); *A61H 2201/50* (2013.01); *A61H 2209/00* (2013.01)

(58) Field of Classification Search
CPC ... A61B 5/1073; A61B 5/0053; A61B 5/4878; A61B 5/1072; A61B 5/1074; A61B 5/1075
USPC ........................................................ 600/587
See application file for complete search history.

(56) References Cited

U.S. PATENT DOCUMENTS

| | | | |
|---|---|---|---|
| 4,013,069 A | 3/1977 | Hasty | |
| 4,086,920 A | 5/1978 | Miniere | |
| 4,338,923 A | 7/1982 | Gelfer et al. | |
| 4,424,806 A | 1/1984 | Newman et al. | |
| 4,762,121 A | 8/1988 | Shienfeld | |
| 4,773,397 A | 9/1988 | Wright et al. | |
| 4,865,020 A | 9/1989 | Bullard | |
| 4,922,893 A | 5/1990 | Wright et al. | |
| 5,014,681 A | 5/1991 | Neeman et al. | |
| 5,089,961 A * | 2/1992 | Coble ................. | A61B 5/02007 600/507 |
| 5,092,317 A | 3/1992 | Zelikovski | |
| 5,117,812 A | 6/1992 | McWhorter | |
| 5,179,941 A | 1/1993 | Siemssen et al. | |
| 5,186,163 A | 2/1993 | Dye | |
| 5,263,473 A | 11/1993 | McWhorter | |
| 5,307,791 A | 5/1994 | Senoue et al. | |
| 5,383,842 A | 1/1995 | Bertini | |
| 5,437,610 A | 8/1995 | Cariapa et al. | |
| 5,496,262 A | 3/1996 | Johnson, Jr. et al. | |
| 5,554,103 A | 9/1996 | Zheng et al. | |
| 5,571,075 A | 11/1996 | Bullard | |
| 5,575,762 A | 11/1996 | Peeler et al. | |
| 5,584,798 A | 12/1996 | Fox | |
| 5,588,955 A | 12/1996 | Johnson, Jr. et al. | |
| 5,591,200 A | 1/1997 | Cone et al. | |
| 5,795,312 A | 8/1998 | Dye | |
| 5,830,164 A | 11/1998 | Cone et al. | |
| 5,840,049 A | 11/1998 | Tumey et al. | |
| 5,843,007 A | 12/1998 | McEwen et al. | |
| 5,891,065 A | 4/1999 | Cariapa et al. | |
| 5,951,502 A | 9/1999 | Peeler et al. | |
| 5,968,073 A | 10/1999 | Jacobs | |
| 6,007,559 A | 12/1999 | Arkans | |
| 6,010,471 A | 1/2000 | Ben-Noon | |
| 6,080,120 A | 6/2000 | Sandman et al. | |
| 6,123,681 A | 9/2000 | Brown, III | |
| 6,129,688 A | 10/2000 | Arkans | |
| 6,135,116 A | 10/2000 | Vogel et al. | |
| 6,179,796 B1 | 1/2001 | Waldridge | |
| 6,231,532 B1 | 5/2001 | Watson et al. | |
| 6,290,662 B1 | 9/2001 | Morris et al. | |
| 6,296,617 B1 | 10/2001 | Peeler et al. | |
| 6,315,745 B1 | 11/2001 | Kloecker | |
| 6,406,445 B1 | 6/2002 | Ben-Nun | |
| 6,436,064 B1 | 8/2002 | Kloecker | |
| 6,440,093 B1 | 8/2002 | McEwen et al. | |
| 6,494,852 B1 | 12/2002 | Barak et al. | |
| 6,544,202 B2 | 4/2003 | McEwen et al. | |
| 6,558,338 B1 | 5/2003 | Wasserman | |
| 6,645,165 B2 | 11/2003 | Waldridge et al. | |
| 6,736,787 B1 | 5/2004 | McEwen et al. | |
| 6,786,879 B1 | 9/2004 | Bolam et al. | |
| 6,846,295 B1 | 1/2005 | Ben-Nun | |
| 6,852,089 B2 | 2/2005 | Kloecker et al. | |
| 6,860,862 B2 | 3/2005 | Waldridge et al. | |
| 6,884,255 B1 | 4/2005 | Newton | |
| 6,893,409 B1 | 5/2005 | Lina | |
| 6,945,944 B2 | 9/2005 | Kuiper et al. | |
| 6,966,884 B2 | 11/2005 | Waldridge et al. | |
| 7,063,676 B2 | 6/2006 | Barak et al. | |
| 7,398,803 B2 | 7/2008 | Newton | |
| 7,637,879 B2 | 12/2009 | Barak et al. | |
| 7,846,114 B2 | 12/2010 | Webster et al. | |
| 7,862,525 B2 | 1/2011 | Carkner et al. | |
| 8,753,300 B2 * | 6/2014 | Deshpande .......... | A61H 9/0078 601/148 |
| 8,827,930 B2 * | 9/2014 | Wekell ................. | A61B 5/0002 600/587 |
| 2002/0091345 A1 | 7/2002 | Hazard | |
| 2003/0208465 A1 | 11/2003 | Yurko et al. | |
| 2004/0171971 A1 | 9/2004 | Ravikumar et al. | |
| 2004/0261182 A1 | 12/2004 | Biggie et al. | |
| 2005/0154336 A1 | 7/2005 | Kloecker et al. | |
| 2005/0222526 A1 | 10/2005 | Perry et al. | |
| 2006/0104824 A1 * | 5/2006 | Schnall .................... | A61B 5/02 417/53 |
| 2006/0161081 A1 | 7/2006 | Barak et al. | |
| 2006/0272719 A1 | 12/2006 | Steinberg | |
| 2007/0049853 A1 | 3/2007 | Adams et al. | |
| 2007/0088239 A1 | 4/2007 | Roth et al. | |
| 2007/0249976 A1 | 10/2007 | Tucker et al. | |
| 2008/0103397 A1 * | 5/2008 | Barak ................. | A61B 5/02007 600/492 |
| 2008/0281240 A1 | 11/2008 | Wright et al. | |
| 2009/0007341 A1 | 1/2009 | Roff et al. | |
| 2009/0056020 A1 | 3/2009 | Caminade et al. | |
| 2009/0145234 A1 | 6/2009 | Gasbarro et al. | |
| 2011/0190675 A1 * | 8/2011 | Vess ..................... | A61H 9/0092 601/152 |
| 2012/0004603 A1 * | 1/2012 | Harari .................. | A61B 5/1075 604/74 |
| 2012/0219432 A1 | 8/2012 | Wright et al. | |
| 2012/0277636 A1 * | 11/2012 | Blondheim et al. .......... 600/595 | |
| 2013/0125613 A1 | 5/2013 | Grotov | |
| 2013/0237889 A1 | 9/2013 | Wright et al. | |
| 2013/0331748 A1 | 12/2013 | Wright et al. | |

FOREIGN PATENT DOCUMENTS

| | | |
|---|---|---|
| GB | 2313784 A | 10/1997 |
| WO | WO 2005/082314 A1 | 9/2005 |
| WO | WO 2007/074451 A2 | 7/2007 |
| WO | WO 2009/076269 A2 | 6/2009 |
| WO | WO 2013/138307 A1 | 9/2013 |
| WO | WO 2014/031409 A1 | 2/2014 |

* cited by examiner

METHODS FOR DETERMINING THE SIZE OF BODY PARTS AS PART OF COMPRESSION THERAPY PROCEDURES

CLAIM OF PRIORITY

This application claims the benefit of U.S. Provisional Application Ser. No. 61/684,720 filed Aug. 18, 2012, the disclosure of which is incorporated by reference herein in its entirety.

BACKGROUND

Diseases such as venous insufficiency, lymphedema, and other edematous conditions can often result in the pooling of bodily fluids in areas of the body distal from the heart. Venous insufficiency can result when the superficial veins of an extremity empty into the deep veins of the lower leg. Normally, the contractions of the calf muscles act as a pump, moving blood into the popliteal vein, the outflow vessel. Failure of this pumping action can occur as a result of muscle weakness, overall chamber size reduction, valvular incompetence, and/or outflow obstruction. Each of these conditions can lead to venous stasis and hypertension in the affected area. Lymphedema, which is swelling due to a blockage of the lymph passages, may be caused by lymphatic obstruction, a blockage of the lymph vessels that drain fluid from tissues throughout the body. This is most commonly due to cancer surgery, general surgery, tumors, radiation treatments, trauma and congenital anomalies. Lymphedema is a chronic condition that currently has no cure.

Fluid accumulation can be painful and debilitating if not treated. Fluid accumulation can reduce oxygen transport, interfere with wound healing, provide a medium that support infections, or even result in the loss of a limb if left untreated.

Compression therapy devices are often used in the treatment of venous insufficiency by moving the accumulated bodily fluids. Additional conditions may also benefit from the use of compression therapy devices. Such devices typically include an air compressor that may blow air through tubes to an appliance such as a sleeve or boot containing a number of separately inflatable cells that is fitted over a problem area (such as an extremity or torso). Such devices may also include pneumatic components adapted to inflate and exhaust the cells, and control circuitry governing the pneumatic components. A therapeutic cycle or protocol may involve, for example, sequential inflation of the cells to a pre-set pressure in a distal to a proximal order, followed by exhausting all the cells in concert.

Effective compression therapy may rely upon the use of the proper equipment and proper therapeutic protocol. The compression sleeve device for treating a limb, for example, may provide a therapeutic amount of pressure to the affected limb if it is properly sized. A sleeve that is too small may be too tight for the patient to wear, and may be uncomfortable. Alternatively, a sleeve that is too large may not be able to attain sufficient pressure against the patent's limb. It would therefore be useful to have a means to determine the correct size of the sleeve for the patient.

SUMMARY

Before the present methods, systems and materials are described, it is to be understood that this disclosure is not limited to the particular methodologies, systems and materials described, as these may vary. It is also to be understood that the terminology used in the description is for the purpose of describing the particular versions or embodiments only, and is not intended to limit the scope.

It must also be noted that as used herein and in the appended claims, the singular forms "a," "an," and "the" include plural references unless the context clearly dictates otherwise. Thus, for example, reference to a "valve" is a reference to one or more valves and equivalents thereof known to those skilled in the art, and so forth. Unless defined otherwise, all technical and scientific terms used herein have the same meanings as commonly understood by one of ordinary skill in the art. Although any methods, materials, and devices similar or equivalent to those described herein can be used in the practice or testing of embodiments, the preferred methods, materials, and devices are now described. All publications mentioned herein are incorporated by reference. Nothing herein is to be construed as an admission that the embodiments described herein are not entitled to antedate such disclosure by virtue of prior invention.

In an embodiment, a method of measuring a volume of at least a portion of a body part includes providing a compression therapy device having an inflatable compression sleeve—the sleeve having at least one compression cell—a source of fluid for inflating the compression sleeve, and a controller for controlling the inflation of the compression sleeve, in which the controller includes at least one sensor associated with the compression sleeve, at least one memory storage device to store a measurement data, at least one communication device, at least one user input interface device, and at least one user output interface device, evacuating, by the controller, the fluid from at least one compression cell until at least one compression cell parameter measured by one or more sensors attains at least one starting compression cell parameter value, introducing a patient body part into the compression sleeve, inflating, by the controller, at least one compression cell with the fluid until at least one controller parameter attains a first pre-set controller parameter value, measuring, by the controller, at least one first compression cell parameter value, and calculating, by the controller, a volume of at least a portion of the patient body part based at least in part on the first compression cell parameter value.

In an embodiment, a method of measuring a volume of at least a portion of a body part includes providing a compression therapy device having an inflatable compression sleeve—the sleeve having multiple compression cells—a source of fluid for inflating the multiple compression cells, and a controller for controlling the inflation of the multiple compression cells, in which the controller includes at least one sensor associated with the compression sleeve, at least one memory storage device to store a measurement data, at least one communication device, at least one user input interface device, and at least one user output interface device, measuring, by the controller, a compression cell parameter associated with each of the multiple compression cells using at least one sensor, evacuating, by the controller, the fluid from the multiple compression cells until the cell parameter associated with each of the multiple compression cells as measured the sensors attains a starting compression cell parameter value for each one of the multiple compression cells, introducing a patient body part into the compression sleeve, inflating, by the controller, each of the multiple compression cells with the fluid until at least one controller parameter attains at least one of a number of first pre-set controller measurement values, measuring, by the controller, a first compression cell parameter value for each of the multiple compression cells, and calculating, by the controller, a volume of at least a portion of the patient body part based at least in part on the cell parameter value of each of the multiple compression cells.

In an embodiment, a method of measuring a circumference of at least a portion of a body part includes providing a compression therapy device having an inflatable compression sleeve—the sleeve having at least one compression cell—a source of fluid for inflating the compression sleeve, and a controller for controlling the inflation of the compression sleeve, in which the controller includes at least one sensor associated with the compression sleeve, at least one memory storage device to store a measurement data, at least one communication device, at least one user input interface device, and at least one user output interface device, evacuating, by the controller, the fluid from at least one compression cell until at least one compression cell parameter measured by one or more sensors attains at least one starting compression cell parameter value, introducing a patient body part into the compression sleeve, inflating, by the controller, at least one compression cell with the fluid until at least one controller parameter attains a first pre-set controller parameter value, measuring, by the controller, at least one first compression cell parameter value, and calculating, by the controller, a circumference of at least a portion of the patient body part based at least in part on the first compression cell parameter value.

BRIEF DESCRIPTION OF THE DRAWINGS

Aspects, features, benefits and advantages of the embodiments described herein will be apparent with regard to the following description, appended claims and accompanying drawings where:

DETAILED DESCRIPTION

For the purpose of this disclosure, the term "compression sleeve" may be defined as an inflatable appliance including one or more individually inflatable chambers or cells used for delivering at least some compressive force to some tissue of a patient to relieve a medical condition. These chambers may also be described as compression cells. The sleeve may encompass one body part such as the chest, or two or more non-contiguous or contiguous body parts such as a combination of foot, ankle, calf (lower leg), and/or thigh (upper leg). Other non-limiting examples of compression sleeves may include appliances to treat the lower arm, the upper arm, the wrist, the hand, a combination of hand/wrist/lower arm/upper arm, chest, single shoulder, back, combination shoulder/chest/back, combination shoulder/chest/back/upper arm, abdomen, buttocks, and genitals. More than one compression sleeve may be worn by the patient at any one time.

For the purpose of this disclosure, the term "compression cell parameter" may be defined as a parameter associated with a physical property of at least one compression cell. Such physical properties may include, without limitation, the shape or size of a compression cell, the strain on a membrane or other structure that defines the physical body of the cell, the pressure within the cell, the volume contained within the cell, and the diameter or circumference of the cell.

For the purpose of this disclosure, the term "compression cell parameter value" may be defined as the measured value of a compression cell parameter. The measurement may be made by one or more sensors alone or in concert with an electronic device. Thus, a compression cell parameter value may include, without limitation, a volume, a pressure, a surface area, and/or a strain measurement of the compression cell body.

For the purpose of this disclosure, the term "controller parameter" may be defined as a factor that may define at least one aspect of a controller or sleeve performance. A controller parameter may include, without limitation, a compression cell inflation time, a compression cell inflation rate, a compression cell deflation time, a compression cell deflation rate, a compression cell evacuation time, a compression cell evacuation rate, a compression cell pressure, a compression cell inflation volume, and/or a compression cell surface deformation.

For the purpose of this disclosure, the term "controller parameter value" may be defined as a value determined by the controller of a controller parameter.

For the purpose of this disclosure, the term "body part" may be defined as one or more contiguous or non-contiguous parts of a human or animal body to which compression therapy may be applied. As one non-limiting example, a body part may include a combination of hand, wrist, lower arm, upper arm, and shoulder.

Although the devices, systems, methods, illustrations, and examples disclosed herein may focus primarily on applications related to human patients, the devices, systems, methods, illustrations, and examples may equally apply to non-human animals that may benefit from an application of compression therapy for veterinary purposes.

As disclosed above, knowledge of the size of a body part undergoing compression therapy may be critical for therapeutic success. In this context, the size of a body part may include, without limitation, circumference, surface area, and/or volume. The measurement of the size may be an absolute value, or may be a value compared to another size measurement. In one embodiment, the size measurement may be compared to a patient's unaffected body part (such as a contralateral leg). In another embodiment, the size measurement may be compared to an average value obtained from some number of other patients. In yet another embodiment, the size measurement may be compared to the size of the patient's body part at some time earlier in the therapy process. In still another embodiment, the size measurement may be compared to a computer model.

The choice of the compression sleeve size may be one example of the use of an absolute measurement of a patient's body part. If a compression sleeve is too small for the body part, the patient may find it difficult to use the sleeve and therefore would be reluctant to comply with the therapy. Alternatively, a sleeve too large for the body part may not provide sufficient pressure against the body part and could therefore result in ineffective therapy. A health care provider may therefore measure the patient's body part prior to the start of compression therapy in order to choose a properly sized compression sleeve. Moreover, as the patient continues with the therapy, the amount of edema present in the body part may be reduced to such an extent that a smaller sleeve may be required to continue delivering proper therapy.

Health care workers could rely upon comparative size measurements for monitoring the progress of the patient's therapy. A decrease in body part size over the course of therapy could indicate that the compression therapy is effective. The health care provider could note this result and recommend maintaining the protocol. Alternatively, if a body part does not show a change in size over the course of the therapy, the health care provider may determine that a different therapy protocol may be required. In addition to health care workers, insurance providers may also wish to document changes in body part size. Since the insurance providers may pay for patient rental of compression therapy devices, the insurance providers may wish to have documented evidence that the therapy is effective.

A patient's body part maybe measured according to any number of methods. A tape measure may be applied at several points of the body part or around the body part and relevant values may be recorded. A disadvantage of this method is that the health care worker may not apply the tape measure consistently to the same parts of the body part or in the same manner. The surface of the body part may be measured optically using a laser or by using multiple photographs or other optical images. Such measurements may rely upon specialized equipment that may not be readily available to health care providers or patients.

In still another example, the body part maybe measured using the compression sleeve. For a circumferential compression cell, as a non-limiting example, the body part enclosed by the cell may reduce the amount of cell inflation due to the body part volume being within the expansion space of the cell. As one measurement example, the volume of an expansion cell may be made with the body part inserted. However, because both the body part and the cell may be compressible and deformable, the simple measurement of the cell volume with the inserted body part may not be accurate. An alternative measurement may be made by comparing the volume of an expansion cell without a body part inserted with the volume of the expansion cell with the body part inserted within it. However, if the initial state of the expansion cell (i.e., without the body part) is not consistent from one measurement to the next, it may be difficult to obtain a consistent value for the body part size. It thus appears that a method for measuring a body part size using compression cell inflation parameters may be improved by using a standardized initial state of the compression cell.

Figure 1A:
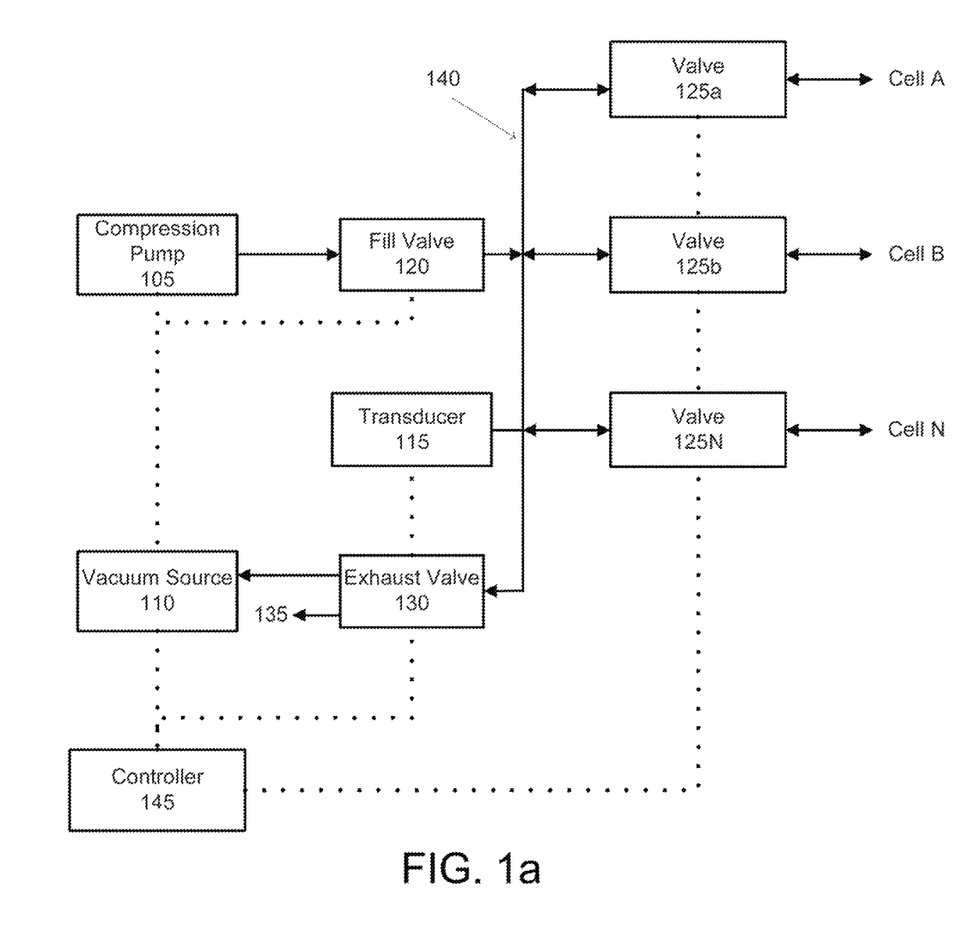
FIGS. 1a,b depict illustrative pneumatic compression therapy systems in accordance with embodiments.
Figure 1B:
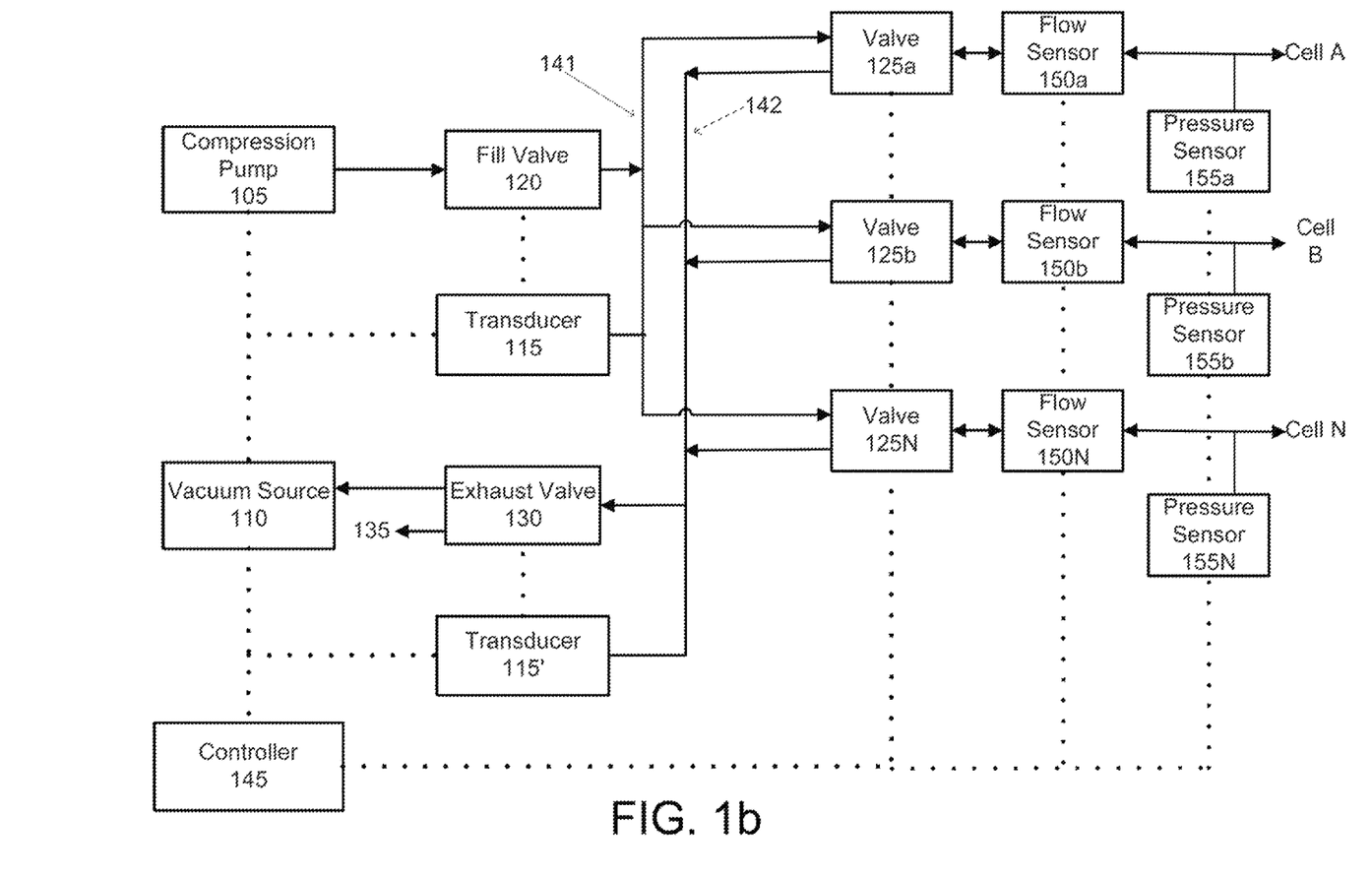

FIGS. 1a,b depict embodiments of a pneumatic compression device. As shown in FIG. 1a, the pneumatic compression device may include a compression pump 105, a fill valve 120, a vacuum source 110, an exhaust valve 130, a transducer 115, a controller 145 and a plurality of cell valves, such as 125a-N. The compression pump 105 may be used to provide a pressurized fluid, including, without limitation, air, nitrogen, or water. The fill valve 120 may be in fluid connection with the compression pump 105 to receive the pressurized fluid. During an inflation period, the fill valve 120 may open to connect the output of the compression pump 105 to a common node or manifold 140. During a deflation period, exhaust valve 130 may open to connect the common manifold 140 to, for example, a vacuum source 110 to depressurize the cells. Alternatively, exhaust valve 130 may be connected to atmosphere 135. Typically, fill valve 120 and exhaust valve 130 may not be open at the same time. However, some modes of use of the compression device may benefit from the fill valve 120 and exhaust valve 130 being open together. Although FIG. 1a illustrates a single exhaust valve 130 capable of connecting to either a vacuum source 110 or the atmosphere 135, it may be appreciated that one exhaust valve may be used to connect the manifold 140 to the vacuum source 110, while a second exhaust valve may be used to connect the manifold 140 to atmosphere 135. Fill valve 120 and exhaust valve 130 may be manually operated, or may be automatically operated by controller 145. In an alternative embodiment, controller 145 may further include one or more communications links to one or more local or remote devices. Such communications links may permit, as one non-limiting example, a physician or therapist to direct, control, or monitor the pneumatic compression device. Additional fill and/or exhaust valves may be associated with the manifold 140. Each of the cell valves 125a-N may be connected to the common manifold 140 on a first side and a corresponding cell on a second side. Each cell valve 125a-N may be used to selectively connect (in an open configuration) or disconnect (in a closed configuration) the corresponding cell to the common manifold 140. Cell valves 125a-N may also be manually operated or automatically operated by controller 145.

The transducer 115 may be connected to and used to monitor the pressure of the common manifold 140. The controller 145 may receive information regarding the pressure detected by the transducer 115. Based on at least the received pressure information, the controller 145 may determine whether to open or close the fill valve 120, the exhaust valve 130, and/or one or more of the cell valves 125a-N.

In an embodiment, illustrated in FIG. 1a, the transducer 115 may have a transfer function associated with it which may be used to determine the input pressure monitored at the common manifold 140.

An additional embodiment is illustrated in FIG. 1b. In this embodiment, a fill manifold 141 may be associated with the fill valve 120 and compression pump 105. A separate exhaust manifold 142 may be associated with the vacuum source 110 and exhaust valve 130. Cell valves 125a-N may be associated with both the fill manifold 141 and exhaust manifold 142. It is understood that cell valves 125a-N in this embodiment may have a 3-way function: open to fill, open to exhaust, and closed. In an alternative embodiment, each cell may have a first valve to connect to the fill manifold 141 and a second valve to connect to the exhaust manifold 142. In the dual manifold embodiment in FIG. 1b, transducer 115, associated with fill manifold 141, may be calibrated with respect to atmosphere by means of a separate shunt valve (not shown) associated either directly with transducer 115 or with the fill manifold 141. Exhaust manifold 142 may also be in communication with its own transducer 115' to monitor the pressure within the exhaust manifold. Transducers 115 and 115' may provide sensor data as well to controller 145.

In addition, each valve 125a-N may be in fluid connection with a flow sensor 150a-N in-line with the connection to its respective cell. Flow sensors 150a-N may provide sensor data as well to controller 145. For example, a flow sensor 150a-N may be used to monitor that its respective valve 125a-N is completely open. If a valve is blocked or otherwise impeded, the fluid flow through it may not match an expected flow profile as determined by controller 145. A flow sensor 150a-N could provide the controller 145 with data to indicate a fault with the associated valve 125a-N. The controller 145 may then be programmed to notify a user of the valve flow fault condition. Additionally, the flow sensors 150a-N may be used to accurately determine the rate of air flow into or from a particular cell, or the total amount of air pumped into (or exhausted from) a cell over a fixed period of time. Based on the data from the flow sensor 150a-N, the fill/exhaust rate for a cell may be adjusted by controller 145 to control the amount of time required for a fill or exhaust step. A clinician developing a particular therapy protocol may then be able to program a fill or exhaust time as part of the protocol. Such time-based programming may be easier for a clinician to use instead of flow rates and volumes.

Additionally, a pressure sensor 155a-N may be associated with each cell to measure the fluid pressure within the cell during its operation. The pressure sensors 155a-N may also provide data to controller 145 so that the controller may be able to control the operation of the compression device. A pressure sensor 155a-N associated with its respective cell, may provide direct indication of a pressurization or depressurization profile of the cell. Alternatively, transducer 115 may measure the pressure of any cell communicating with common manifold 140 by means of its respective valve 125a-N. Controller 145 may compare an individual cell pressure against a pre-programmed cell pressure profile. If a cell is unable to sustain an expected pressure, a leak condition may be determined. The controller 145 may then be programmed to notify a user of the leak condition.

Although FIG. 1a does not explicitly illustrate the use of either flow or pressure sensors between the valves 125a-N and their respective cells, it may be appreciated that either flow sensors, pressure sensors, or both types of sensors may be included in alternative embodiments. Similarly, although FIG. 1b illustrates the use of such sensors, it should be understood that other embodiments may lack either one or both types of sensors.

The pneumatic compression device may be operated to provide a variety of therapeutic protocols. A therapeutic protocol may be defined as a specific sequence of operations to inflate (fill) and deflate (exhaust) one or more cells while they are in contact with a patient. Therapeutic protocols may include, in a non-limiting example, a list of a sequence of cells to be activated, an inflation or deflation pressure measure for each cell, an amount of time during cell inflation or deflation, and a time between sequential cell activation.

Prior to the start of a therapeutic protocol, an initialization sequence may occur. In one example of an initialization sequence, fill valve 120 may be closed, thereby isolating the compression pump 105 from a manifold (either 140 or 141), and exhaust valve 130 may be opened to atmosphere 135. The cell valves 125a-N may then be opened thereby placing each cell in fluid communication with either the common manifold 140 or exhaust manifold 142. Alternatively, exhaust valve 130 may be opened to vacuum source 110 to permit rapid evacuation of the cells. The controller 145 may determine whether a minimum pressure threshold has been reached based on information received from the transducer 115 (for a common manifold configuration) or from transducer 115' (for a dual manifold configuration). The controller 145 may also receive sensor data from the cell specific pressure sensors 155a-N. In one embodiment, when the minimum pressure threshold is reached, the controller 145 may send operation commands to exhaust valve 130 to close. In another embodiment, the controller 145 may also provide operation commands to the cell valves 125a-N to close. In yet another embodiment, the controller 145 may initiate a therapeutic protocol. It may be appreciated that the initialization sequence may occur while the cells are in contact with the patient, before the cells are affixed onto the patient, or after a protocol has been completed.

A protocol may incorporate one or more cell fill phases. As a non-limiting example of such a fill phase, the following operating sequence may occur. One or more cell valves 125a-N may be opened along with the fill valve 120 thereby allowing the one or more cells to be in fluid communication with the compression pump 105. In an embodiment incorporating a common manifold 140, one or more of the cell valves 125a-N may open to the common manifold. In an embodiment having independent fill 141 and exhaust 142 manifolds, one or more of the cell valves 125a-N may be configured to open the cells to communicate with the fill manifold 141 only. In an embodiment, a cell valve, such as 125a, connected to a cell affixed to a distal portion of the patient, may be opened or remain open to the fill manifold 141 or common manifold 140 for inflation while cell valves associated with more proximal cells are closed to that manifold. The cell (e.g., cell A) connected to the open cell valve (e.g., 125a) may inflate as a result of being connected to the pressurized fluid from the compression pump 105. The cell pressure may be monitored by the controller 145 via the transducer 115 and/or a pressure sensor 155a associated specifically with that cell.

In an embodiment, the amount of pressure sensed by the transducer 115 may differ from the cell pressure at a particular cell. For example, pressure losses may occur between the transducer 115 and a cell. Accordingly, the controller 145 may access a lookup table to determine the threshold at which the pressure sensed by the transducer 115 is appropriate to close the cell valve 125a-N corresponding to the cell.

In another embodiment of a fill phase, an opened cell valve, such as 125a, may be modulated to control the fill rate of the corresponding cell. The opened cell valve may be modulated based on time and/or pressure. For example, a cell valve that is being modulated on a time basis may be opened for a first period of time and closed for a second period of time as the cell is inflating. Alternately, a cell valve that is being modulated on a pressure basis may be opened while the cell pressure increases and closed for a period of time during the inflation cycle. The pressure increase may be determined by measuring an initial cell pressure before opening the cell valve and the cell pressure as the cell valve is open. When the difference between the initial cell pressure and the inflating cell pressure is substantially equal to a specific value, the cell valve may be closed. The duty cycle at which the cell valve is modulated may be any value and may be specifically programmed by a user or clinician. The controller 145 may determine when to open and close the cell valve. For pressure-based modulation, any one or more of transducer 115 or cell specific pressure sensors 155 may provide pressure data to the controller 145 to assist in determining when to open and/or close the cell valve during modulation.

Modulation may be performed to ensure that the cell pressure does not increase too quickly for a given protocol. For example, a lymphedema patient may be treated with a protocol requiring slowly inflating and deflating cells. Alternatively, an arterial patient may require a protocol capable of rapid inflation and deflation cycles. Moreover, cells may be of varying size. For example, cells in a device designed for a child may be smaller than cells in a device designed for an adult. However, the compression pump 105 may have a relatively fixed flow rate. As such, modulation may be used to ensure that cell inflation is performed at a proper rate.

In an alternate embodiment, a cell valve, such as 125a, may include a variable aperture, which may be used to restrict the rate at which the pressure increases in the corresponding cell. A flow sensor such as 150a may monitor the fluid flow rate into the cell. The data from the flow sensor may be provided to controller 145 so that the controller may be able to adjust the aperture in the cell valve. In another embodiment, a cell valve such as 125a may incorporate a one-way valve. For example, if valve 125a is opened to allow cell A to be filled by common manifold 140 or fill manifold 141, and then valve 125b is opened to allow cell B to be pressurized, a one-way valve incorporated in valve 125a will prevent transient depressurization of cell A when valve 125b is opened to initially evacuated cell B. In another alternate embodiment, a compression pump 105 that operates with a variable flow rate may be used. Additional methods of modulating pressure may also be performed and will be apparent to one of ordinary skill in the art based on this disclosure.

When the cell reaches an appropriate pressure, the controller 145 may close the cell valve 125a corresponding to the cell.

A protocol may also incorporate one or more cell exhaust phases. As a non-limiting example of such an exhaust phase, the following operating sequence may occur. One or more cell valves 125a-N may be opened along with the exhaust valve 130, thereby allowing the one or more cells to be in fluid communication with either the vacuum source 110 or atmosphere 135. In an embodiment incorporating a common manifold 140, one or more of the cell valves 125a-N may open to the common manifold. In an embodiment having an independent fill manifold 141 and exhaust manifold 142, the one or more cell valves 125a-N may be configured to open the cells to communicate with the exhaust manifold 142 only. In an embodiment, a cell valve, such as 125a, connected to a cell affixed to a distal portion of the patient, may be opened or remain open to the exhaust manifold 142 or common manifold 140 for deflation while cell valves associated with more proximal cells are closed to that manifold. The cell (e.g., cell A) connected to the open cell valve (e.g., 125a) may deflate as a result of being connected to the vacuum source 110 or atmosphere 135. The cell pressure may be monitored by the controller 145 via transducer 115 for a common manifold configurations or transducer 115' for independent manifold configurations, a pressure sensor 155a associated specifically with that cell, or by both.

In an embodiment, the amount of pressure sensed by the transducer 115 or transducer 115' may differ from the cell pressure at a particular cell. For example, pressure losses may occur between the transducer 115 (or 115') and a cell. Accordingly, the controller 145 may access a lookup table to determine the threshold at which the pressure sensed by the transducer 115 (or 115') is appropriate to close the cell valve 125a-N corresponding to the cell.

In another embodiment of an exhaust phase, an opened cell valve, such as 125a, may be modulated to control the exhaust rate of the corresponding cell. The opened cell valve may be modulated based on time and/or pressure. For example, a cell valve that is being modulated on a time basis may be opened for a first period of time and closed for a second period of time as the cell is deflating. Alternately, a cell valve that is being modulated on a pressure basis may be opened while the cell pressure decreases and closed for a period of time during the exhaust cycle. The pressure decrease may be determined by measuring an initial cell pressure before opening the cell valve and the deflated cell pressure as the cell valve is open. When the difference between the initial cell pressure and the cell pressure is substantially equal to a specific value, the cell valve may be closed. The duty cycle at which the cell valve is modulated may be any value and may be specifically programmed by a user or clinician. The controller 145 may determine when to open and close the cell valve. For pressure-based modulation, any one or more of transducers 115, 115', or cell specific pressure sensors 155a-N may provide pressure data to the controller 145 to assist in determining when to open and/or close the cell valve during modulation.

Modulation may be performed to ensure that the cell pressure does not decrease too quickly, which could cause a reverse gradient. Moreover, cells may be of varying size. For example, cells in a device designed for a child may be smaller than cells in a device designed for an adult. However, the vacuum source 110 may have a relatively fixed flow rate, and venting to atmosphere 135 may occur due to unregulated, passive exhaust. As such, modulation may be used to ensure that cell deflation is performed at a proper rate.

In an alternate embodiment, a cell valve, such as 125a, may include a variable aperture, which may be used to restrict the rate at which the pressure decreases in the corresponding cell. A flow sensor such as 150a may monitor the fluid flow rate into the cell. The data from the flow sensor may be provided to controller 145 so that the controller may be able to adjust the aperture in the cell valve. In another embodiment, a cell valve such as 125a may incorporate a one-way valve. For example, if valve 125a is opened to allow cell A to be evacuated by exhaust manifold 142, and then valve 125b is opened to allow cell B to be evacuated, a one-way valve incorporated in valve 125a will prevent transient re-pressurization of cell A when valve 125b is opened to previously pressurized cell B. In another alternate embodiment, a vacuum source 110 that operates with a variable flow rate may be used. Additional methods of modulating pressure may also be performed and will be apparent to one of ordinary skill in the art based on this disclosure.

When the cell reaches an appropriate pressure, the controller 145 may close the cell valve 125a corresponding to the cell.

It may be appreciated that a therapeutic protocol may be composed of any variety of sequences of cell inflation and deflation steps. Cells may be inflated and deflated in a specific order, and multiple cells may be inflated or deflated either in synchrony or in a staggered fashion. The cells may be held at a particular inflation or deflation pressure for a specific amount of time. In addition, a specific protocol may be repeated with some lag time between repeats. Alternatively, a first protocol may be followed by a second and different protocol.

In one embodiment of a protocol, a plurality of cell valves 125a-N may be opened simultaneously to inflate the plurality of respective cells simultaneously. As the pressure in each cell surpasses a corresponding threshold, the controller 145 may close the cell valve 125a-N for the cell. The pressure thresholds for all the cells may be identical or they may differ. For example, the pressure threshold for a cell at a distal position on a patient may be higher than a cell more proximally located. As a result, a pressure gradient may be developed by the cells from a greater pressure at the distal point, to a lesser pressure at the proximal point. The cells may then be deflated simultaneously until they all reach an ambient pressure. Alternatively, only selected cells may be deflated.

In an another embodiment of a protocol, the cell valves 125a-N may not be opened simultaneously when the cells are deflated, but rather may be opened in a staggered fashion. In an embodiment based on the common manifold configuration, fill valve 120 may be closed, and exhaust valve 130 may be opened to either the vacuum source 110 or to atmosphere 135. A first cell valve, such as 125$a$, may be opened to release the pressure in the corresponding cell. After a short period of time elapses, such as about 1 second, a second cell valve, such as 125$b$, may be opened to release the pressure in the corresponding cell. The process may be repeated until each cell valve 125$a$-N has been opened.

In an embodiment of a protocol using modulation, a plurality of cell valves 125$a$-N may be modulated simultaneously. At any given time, one or more cell valves may be opened and/or closed according to a modulation schedule. For example, for a time-based modulation scheme having a 50% duty cycle, half of the cell valves 125$a$-N may be open and half of the cell valves may be closed at any time.

Figure 2:
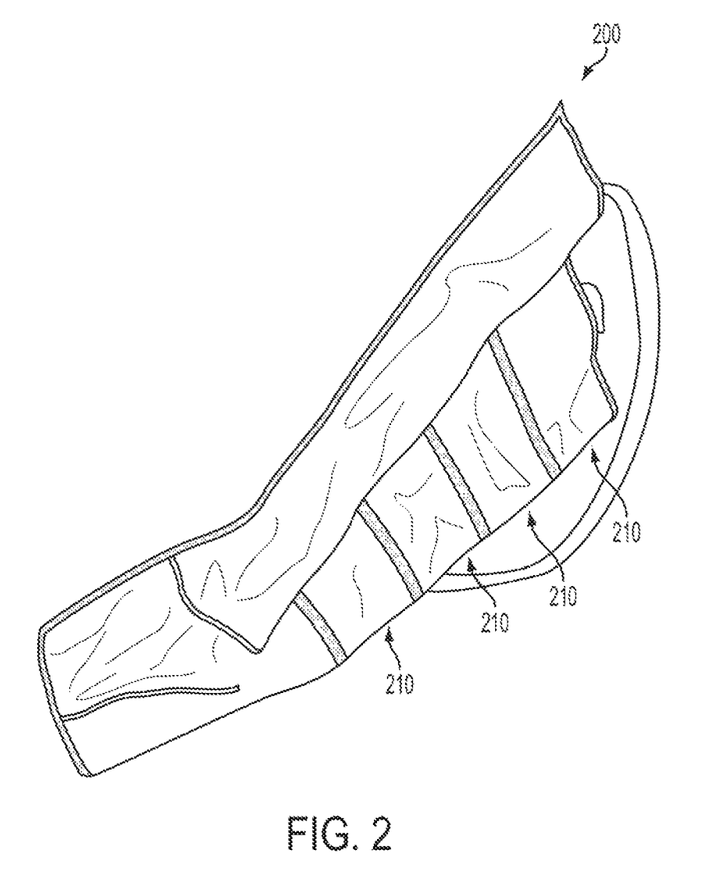
FIG. 2 depicts an illustrative compression therapy system sleeve with compression cells in accordance with some embodiments.

FIG. 2 illustrates an embodiment of a compression sleeve 200 that may be used as part of a compression therapy protocol. While the illustrated sleeve 200 may be used for compression therapy of a foot/calf/thigh, it is understood that an equivalent device may be used for similar therapy of a hand/wrist/lower arm/upper arm/shoulder, or other body parts for which such therapy may be recommended. Compression sleeve 200 may include one or more individually inflatable compression cells 210 which may be disposed along an extent of the sleeve. The compression cells 210 may comprise any of a variety of geometries, including, but not limited to, annular (around an axis of a body part), longitudinal (along an axis of a body part), and pillow-shaped. The compression cells 210 may be inflated with a fluid, such as air, by the controller 145. Alternatively, the fluid within a cell 210 may be actively evacuated by the controller 145 through the use of a vacuum system, or the air may be passively released from the cells (deflation) under control by the controller. The cells 210 may be inflated, deflated, or evacuated in concert or individually according to the protocol executed by the controller 145.

Figure 3:
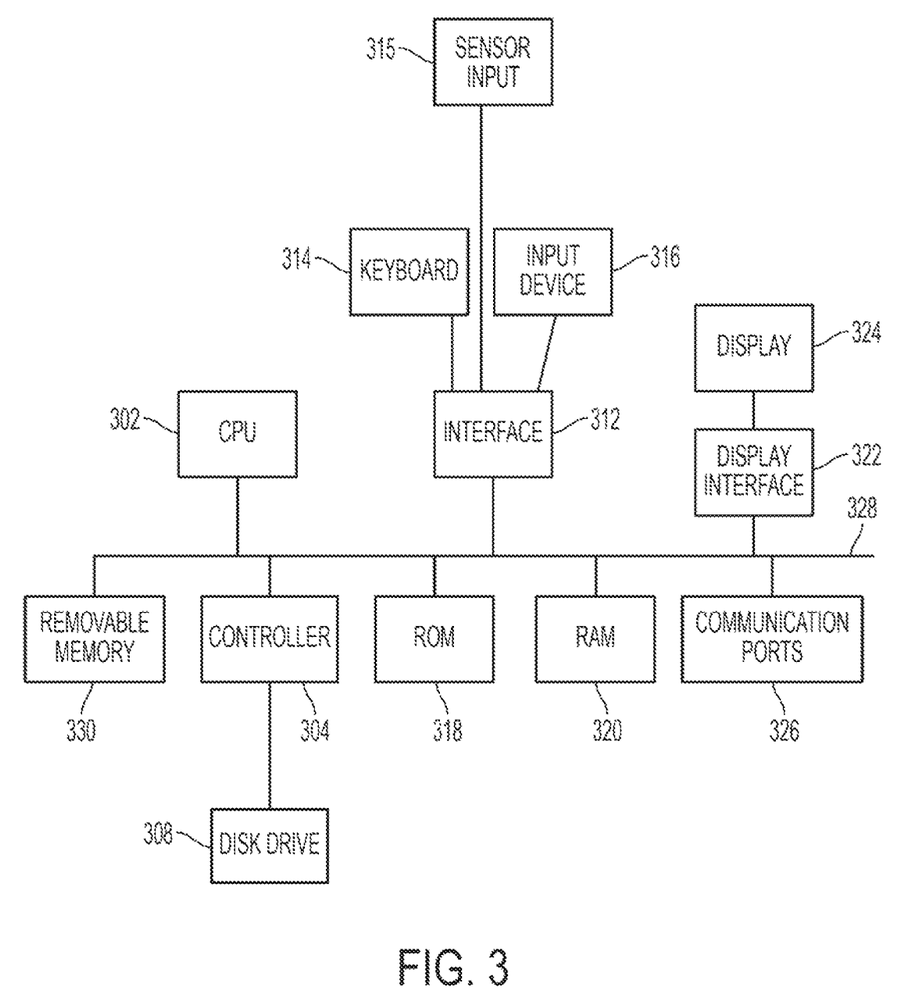
FIG. 3 is a block diagram illustrative of hardware that may be used to contain or implement program instructions in accordance with an embodiment.

FIG. 3 is a block diagram of an embodiment of hardware that may be used to contain or implement program instructions for controller 145. Some or all of the below-described hardware may be incorporated in the controller 145. Referring to FIG. 3, a bus 328 may serve as the main information highway interconnecting the other illustrated components of the hardware. CPU 302 is the central processing unit of the system, performing calculations and logic operations required to execute a program. Read only memory (ROM) 318 is one example of a static or non-transitory memory device, and random access memory (RAM) 320 is one example of a transitory or dynamic memory device.

A controller 304 may interface the system bus 328 with one or more optional disk drives 308. These disk drives may include, for example, external or internal DVD drives, CD ROM drives, or hard drives.

Program instructions may be stored in the ROM 318 and/or the RAM 320. Optionally, program instructions may be stored on a computer readable medium such as a compact disk or a digital disk or other recording medium, a communications signal or a carrier wave. Additionally, operational therapy data may be stored on a removable memory devices 330 that may include, as non-limiting examples, a removable disc, a removable card, a removable memory stick, a flash drive, a removable SIM chip, a writable CD-ROM or DVD disk, and/or a miniature data tape. Such devices may be used to transfer data from the controller to another data receiving device such as a home computer.

An optional display interface 322 may permit information from the bus 328 to be displayed on the display 324 in audio, graphic or alphanumeric format. Additional output interface devices may include a printer, a barcode printer, an LCD panel device, a touch screen device, an audio device, an LED panel, an OLED panel device, one or more individual LEDs, either as separate displays or grouped together, and a haptic device. Communication with external devices may occur using various communication ports 326. For example, communication with the fill valve 120, exhaust valve 130, and/or the cell valves 125$a$-N may occur via one or more communication ports 326. Controller 145 may also provide command data over communication ports 326 to valves 120, 130, and 125$a$-N to direct their respective operations.

In addition to the components disclosed above, the hardware may also include an interface 312 which allows for receipt of data from input devices such as a keyboard 314 or other input devices 316 such as a touch screen, a mouse, remote control, pointing device, pushbutton, haptic device, a voice recognition device, a proximity sensor, a motion detection sensor, a multi-axis accelerometer, a directional pad, and/or joystick. In addition, transducers 115 and 115', pressure sensors 155$a$-N, flow sensors 150$a$-N, as well as sensors communicating data related to the change in shape or volume of the cells, cell or sleeve temperatures, or sensors to detect the pulse associated with a body part inserted into a sleeve may communicate sensor input 315 through interface 312 to bus 328.

In an embodiment, the controller 145 may store and/or determine settings specific to each cell. For example, the controller 145 may determine one or more pressure thresholds for each cell. Moreover, the controller 145 may prevent the pneumatic compression device from being used improperly by enforcing requirements upon the system. For example, the controller 145 may be programmed so that distal cells in a therapeutic protocol are required to have higher pressure thresholds than proximal cells. The controller may override instructions received from a user via the user interface that does not conform to such pressure threshold requirements. In an embodiment, the pressure thresholds of one or more cells may be adjusted to meet the pressure threshold constraints.

In a further embodiment, controller 145 may provide a compression device user with an interface to permit the user to program the controller to provide a variety of therapeutic protocols for patients. The interface may be displayed on the control display, such as a flat panel display. Input devices such as a mouse, keypad, or stylus may be used by the user to provide data to define a particular therapeutic protocol. In addition, a push-button device can be activated by a user to indicate that data from the controller may be transmitted to a receiving unit, such as a computer, cell phone, or wireless hot-spot. The controller may record the protocols on a memory or disk device for future use. In one embodiment of the controller, a user may be presented with a list of previously stored therapeutic protocols from which to choose for a particular patient. In another embodiment, a user may define a therapeutic protocol for a patient on an as-needed basis. In another embodiment, a user may choose a stored protocol and modify it.

In addition to storing protocols, the controller 145 may also record sensor readings obtained during a particular therapy session. Such sensors may include pressure sensors, timing sensors, fluid flow sensors, temperature sensors, inflatable cell material deformation sensors, and others. Sensor readings may include, without limitation, the time a sensor reading is made, cell pressures, cell volumes, cell inflation data, air or vacuum air flow values, and/or temperatures taken from an interior of the sleeve or compression device. The controller may also record patient related data, such as blood pressure, EKG, or blood oxygen saturation levels measured during a therapeutic session, as well as a date and time for the session. The controller may also record therapy notes entered by the user.

Although not illustrated in FIG. 3, controller 145 may also include a number of communications interfaces to a wireless local area network, a localized personal area network (such as a Bluetooth® connection or ZigBee® connection), or a telephony device. Such communication devices may include, without limitation, an Ethernet connection device connected to a computing device, an infrared connecting device connected to a computing device, and a serial connection device connected to a computing device. Telephony devices may include, without limitations, cell phones, landline phones, voice modems, TRx devices, fax machines, and other communications devices based on telephone technology. Such communication interfaces may permit the controller to be monitored remotely by a clinician to obtain performance data or patient compliance data. Such communication interfaces may also permit a remote clinician to program the controller. In one embodiment, a cell phone may have an application that may bring up a user-friendly programming interface to permit ease of reprogramming. Alternatively, a remote computer may display a web-enabled display for programming, data assessment, and/or analysis.

Figure 4:
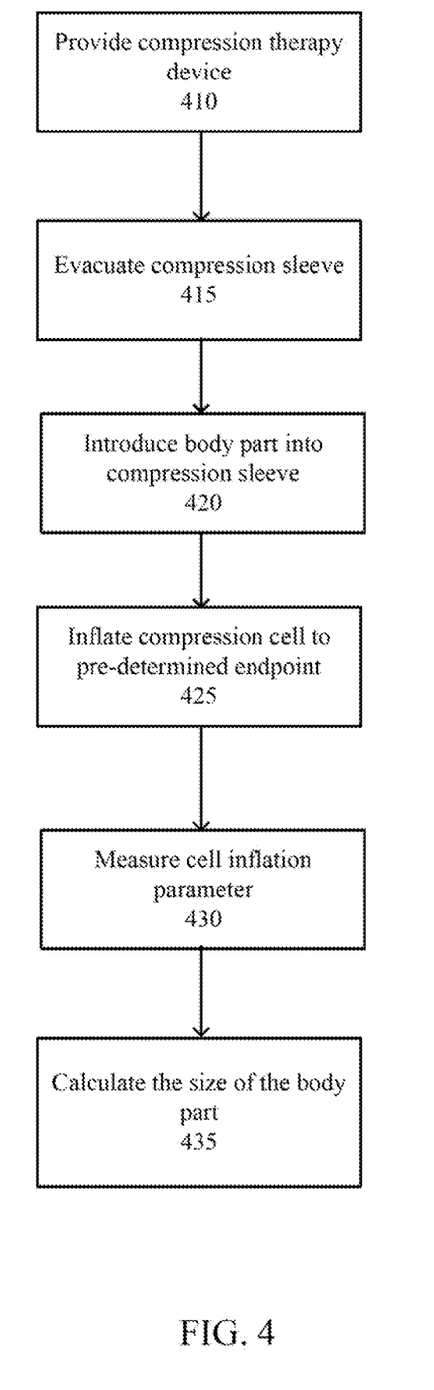
FIG. 4 is a flow chart illustrative of a method to determine the size of body parts as part of compression therapy procedures in accordance with an embodiment.

FIG. 4 discloses a flow chart of one embodiment of a method for measuring the size of a body part to receive compression therapy. A compression therapy device, as substantially disclosed above, may be provided 410, for example to a patient. The compression therapy device may include an inflatable compression sleeve comprising one or more individually inflatable compression cells, a source of fluid—such as a gas—for inflating the sleeve or cells, and a controller unit to control the inflation and deflation of the sleeve and/or the individual cells comprising the sleeve. The controller may include one or more sensors associated with the sleeve, sensors associated with the inflation and deflation devices for the sleeve, at least one non-transitory memory device, and at least one communication device. The controller may also include user input devices.

Before the body part measurement is made, the controller may evacuate the fluid (such as air) from the sleeve or cells 415. One or more compression cell parameters related to the physical state of the compression cell may be measured by the one or more sensors in functional communication with the compression cell or cells. The one or more sensors may include, without limitation, a sensor to measure the pressure within one or more compression cells, a sensor of fluid flow rate into or out of the one or more cells, and a sensor to measure the deformation of the material providing the surface of the one or more cells. Such deformation sensor may include, as a non-limiting example, a strain sensor fixed onto the surface of the cell. The compression cell parameters may include, without limitation, one or more of the cell pressure, the cell volume, and the cell surface deformation. A compression cell may be monitored for one or more of these parameters. The compression cells may be evacuated until the compression cell parameter associated with each cell attains one or more starting compression cell parameter values. The one or more starting compression cell parameter values may be stored in the controller in any one or more memory locations, such as in RAM, ROM, a disk drive, or a removable memory device. Alternatively, a health care provider, such as a therapist, physician, or nurse, may program the controller with the one or more starting values either through a user input device or via a communication port, such as through a wireless device or cell phone.

As illustrated in FIG. 2, a sleeve may include one or more individually inflatable compression cells. It should be understood that the starting compression cell parameter value of any one cell may be essentially identical to or different from the starting compression cell parameter value of any other cell. Further, different cells may be monitored for different parameters. Thus, during the initial cell evacuation step, the pressure in one compression cell may be monitored while the surface deformation or strain may be monitored in a second cell. Additionally, while several cells may be monitored for the same parameter, such as pressure, the starting parameter value may differ between the cells. As one non-limiting example, the starting compression cell parameter value may be a pressure of about −20 mm Hg, about −40 mm Hg, about −60 mm Hg, about −80 mm Hg with respect to atmospheric, or any value therebetween.

After the sleeve has been evacuated so that the sleeve or compression cells have attained the starting compression cell parameter values, the patient may then introduce the body part or parts into the sleeve prior to the start of the measurement process 420. As disclosed above, one or more parts of the patient's body may be introduced into the sleeve depending on the nature of the compression therapy. Thus, the body parts may include one or more of a finger, a hand, a wrist, a lower arm, an upper arm, a shoulder, a chest, an abdomen, a groin, a hip, a buttock, a thigh, a lower leg, a calf, an ankle, a foot, or a toe. In one embodiment, the compression sleeve and controller together may incorporate sensors and methods to verify that the patient has properly introduced his or her body parts into the sleeve and that the sleeve has been properly adjusted for correct fitting for the therapy.

Once the sleeve has been properly placed around the body part, the controller may control the inflation of the sleeve or compression cells with the inflation fluid (such as air) until at least one controller parameter attains a pre-set parameter value 425. This pre-set value may represent an endpoint for this inflation step. The controller parameter may include any factor that may define at least one aspect of the controller or sleeve performance. A controller parameter may include, without limitation, a compression cell inflation time, a compression cell inflation rate, a compression cell pressure, a compression cell inflation volume, or a compression cell surface deformation.

As one non-limiting example, the controller may inflate a compression cell at a specific inflation rate for a pre-set period of time. Examples of the pre-set time may include, without limitation, about 20 seconds, about 30 seconds, about 40 seconds, about 50 seconds, about 1 minute, or a time between any two of these values. In another non-limiting example, the controller may inflate a compression cell at a specific inflation rate until the cell attains a pre-set pressure. Examples of the pre-set pressure may include, without limitations, about 10 mmHg above atmosphere, about 20 mmHg above atmosphere, about 30 mmHg above atmosphere, about 45 mmHg above atmosphere, about 60 mmHg above atmosphere, or a pressure between any two of these values. In still another non-limiting example, the controller may ramp the inflation rate from a first value to a second value until the cell covering attains a pre-set strain value.

It may be understood that multiple compression cells may be inflated, either synchronously or asynchronously, and that the conditions for stopping the inflation process may differ between the cells. For example, one cell may be inflated until it attains a pre-set pressure, while a second cell may be inflated for a set period of time. Additionally, multiple cells may be inflated based on the same controller parameter, such as pressure, but the pre-set controller parameter value may differ between the cells. One cell, as one non-limiting example, may be inflated until it attains a pressure of about 30 mmHg above atmosphere while a second cell may be inflated until it attains a pressure of about 20 mm Hg. The one or more pre-set controller parameter values may be stored in the controller in any one or more memory locations, such as in RAM, ROM, a disk drive, or a removable memory device. Alternatively, a health care provider, such as a therapist, physician, or nurse, may program the controller with the one or more pre-set controller values either through a user input device or via a communication port, such as through a wireless device or cell phone.

A compression cell parameter may be measured for each compression cell to provide a compression cell parameter value 430 for each cell. Such measurement may be made before, during, and/or after the inflation step. A single measurement of the compression cell parameter value for the one or more inflated compression cells may be made. Alternatively, the compression cell parameter measurement may be made over the period of time during which the inflation step occurs. Non-limiting examples of compression cell parameters may include a pressure within a compression cell, a volume of a compression cell, and a measurement of a deformation of a compression cell.

Once the controller has measured the one or more compression cell parameter values, the controller may then calculate the size of the body part inserted into the sleeve 435. In one non-limiting example, the volume measurement may be based at least in part on the final pressure attained in one or more cells after a fixed inflation time. In another non-limiting example, the volume may be based at least in part on the time required for one or more compression cells to attain a fixed pressure. In yet another non-limiting example, the size of the body part may be determined based at least in part on the volume of one or more cells after a fixed inflation time. In still another non-limiting example, the size of the body part may be determined based at least in part on the time required to inflate the cell to a specified cell surface strain value. It may be appreciated that the value of one or more compression cell parameters may be used in the determination of the size of the body part inserted into the sleeve. It may also be understood that a "local" body part size may be determined for the body part adjacent to a single compression cell. Alternatively, the entire body part may be measured based at least in part on the compression cell parameters of all the cells, or some subset of cells, taken together.

The body part size, either as tissue volume or circumference, may be calculated by the controller according to any of a number of methods. In one non-limiting example, the controller may have a look-up table of values to which it may compare the measured compression cell parameter values. The look-up table may be based on average values of measured body parts of a number of patients. Alternatively, the look-up table values may be based on a standardized physical model, such as wooden or rubber model of a limb. In yet another embodiment, the look-up table may have values based on mathematical models of the body part or parts under therapy. The look-up table may also have entries based on the size of the sleeve, such as a small, medium, large, or extra-large sleeve. The look-up table may have entries based on the sleeve size, such as by the length or the volume of the body part that can be inserted into the sleeve.

The table values may also categorize the sleeve in terms of pediatric, adolescent, and adult sizes. It may be understood that a measured compression cell parameter may have a value not explicitly provided by the look-up table. The controller may then use a standard interpolation technique to calculate a body part size based on the values provided in the look-up table.

The controller may also calculate the body part volume or circumference based on the one or more compression cell parameter values according to a mathematical model of the body part under therapy.

In one embodiment, the look-up table, or mathematical model may be stored in a memory location in the controller. The one or more look-up table or mathematical model values may be stored in the controller in any one or more memory locations, such as in RAM, ROM, a disk drive, or a removable memory device. In another embodiment, a health care provider, such as a therapist, physician, or nurse, may program the controller with the one or more look-up table or mathematical model values either through a user input device or via a communication port, such as through a wireless device or cell phone. In yet another embodiment, the look-up table or mathematical model values may be programmed in a memory component housed within the sleeve itself. Such a memory component (non-limiting examples being a ROM, a flash drive, and/or an RFID active memory device) may be accessible to the controller electronics through an electronic connection, including, but not limited to, a direct electrical data line, an optical fiber line, a serial communication line, and/or a parallel communication line. In another embodiment, the controller may access the memory component over a wireless connection which may include, without limitation, an RF communication connection, and/or an IR communication connection.

As disclosed above, in one embodiment, the volume or circumference of a body part placed within the compression sleeve may be measured by evacuating the cells in the sleeve to a known state, inflating the sleeve until a controller parameter attains a first set value, and measuring a sleeve-related parameter. In another embodiment, one or more compression cells may be evacuated or deflated from a pressurized state characterized by the first set parameter value or values until they attain a second set parameter value or values. The compression cell parameters may then be measured before, during, and/or after an evacuation or deflation step and the values may then be used, at least in part, for calculating the body part size. For example, the first set parameter may be a fixed inflation time, and the second set parameter may be a fixed deflation time. Alternatively, the second set parameter may differ from the first set parameter. In a non-limiting example, the first set parameter may be a fixed compression cell pressure, while the second parameter may be a fixed evacuation time. The compression cell parameter measured as part of a deflation step may be the same as or different from the compression cell parameter measured as part of an inflation step. Thus, as a non-limiting example, the volume of one or more compression cells may be measured after an inflation step, while the strain on the compression cell surface may be measured for one or more compression cells after a deflation step. Additionally, it is understood that the compression cell parameter measured for one compression cell may be the same as or different from the cell parameter measured for a second compression cell after the deflation step.

It may be understood that an evacuation rate or time may refer to the rate or time of evacuation of air from one or more compression cells under the power of an evacuation device such as a vacuum pump. Thus, evacuation may comprise an active process of removing air from the cells (a zero-order process). Deflation, in contrast, may comprise a passive process in which the air leaves the one or more compression cells under the force of the pressure difference between atmosphere and the cell pressure (a first-order process). Thus, although a deflation step has been disclosed above, it should be understood that the step may incorporate evacuation instead of deflation. It may also be understood that the initial step of evacuating the sleeve and/or cells until the one or more compression cells attain a starting compression cell parameter value may be replaced with deflating the sleeve and/or cells. Further, individual cells may be deflated or evacuated during this initial step.

In an alternative embodiment, one or more compression cells may be inflated from a first pressurized state characterized by a first set parameter value or values to a second pressurized state until they attain a second set parameter value or values. The compression cell parameters may then be measured before, during, and/or after a second inflation step, and the values may then be used, at least in part, for calculating the body part size. For example, the first set parameter may be a first fixed inflation time, and the second set parameter may be a second fixed inflation time. Alternatively, the second set parameter may differ from the first set parameter. In a non-limiting example, the first set parameter may be a fixed compression cell pressure, while the second parameter may be a fixed inflation time. The compression cell parameter measured as part of a second inflation step may be the same as or different from the compression cell parameter measured as part of a first inflation step. Thus, as a non-limiting example, the volume of one or more compression cells may be measured after a first inflation step, while the strain on the compression cell surface may be measured for one or more compression cells after a second inflation step. Additionally, it is understood that the compression cell parameter measured for one compression cell may be the same as or different from the cell parameter measured for a second compression cell after a second inflation step.

It may be appreciated that a measurement of the volume or circumference of one or more body parts may be calculated based on compression cell parameter values obtained from any number of inflation and or deflation/evacuation steps from one known sleeve and/or compression cell state to another, as disclosed above. Such multiple steps may be used to obtain greater statistical accuracy and precision for the body part measurement. For example, the compression cells may be inflated from a first known state to a second known state during which a first set of cell parameters may be measured, the cells may be deflated/evacuated to the first state, and then re-inflated back to the second state during which the same first set of cell parameters may be measured. This series of inflation steps and deflations/evacuation steps may be performed multiple times to obtain average cell parameter values. Alternatively, the cells may be inflated from a first state to a second state while measuring a first set of parameters, deflated/evacuated to the first state, and then re-inflated to the second state while measuring a second set of parameters. Such a method may allow a consistency check between a first calculated body part size and a second calculated body part size.

The values associated with the one or more second set parameter values may be stored in a memory location in the controller. The one or more second set parameter values may be stored in the controller in any one or more memory locations such as in RAM, ROM, a disk drive, or a removable memory device. Alternatively, a health care provider, such as a therapist, physician, or nurse, may program the controller with the one or more second set parameter values either through a user input device or via a communication port, such as through a wireless device or cell phone.

It may be appreciated that the measurement of the cell parameters to determine the limb size may be made at any time before, during, and/or after the therapeutic protocol has been initiated. For example, once the sleeve and the one or more compression cells have been evacuated to the starting compression cell parameter value or values, the one or more cells can be inflated to a pre-set controller condition and the cell parameter values may be measured before the start of the therapy. The therapy may then be initiated. At any time during the therapy, the cells may be inflated or deflated to one or more pre-set controller conditions and the cell parameter values may be measured. In this manner, the body part may be assessed during the therapy. A similar process (inflation or deflation of one or more cells to set controller conditions) may then be used at the end of the therapy session to determine if any change in limb size has occurred due to the therapy.

It may further be appreciated that the methods disclosed above may be used to measure either a body part volume, circumference, or surface area depending on the techniques used to analyze the measured compression cell values. It may also be appreciated that the volume, circumference, and/or surface area of the entire body part or only sections of the body part may be measured depending on the number of cells used in the measurement method and the analysis of their parameter values.

It will be appreciated that the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which are also intended to be encompassed by the following claims.

What is claimed is:

1. A method of electronically measuring a volume of a bodypart using a compression therapy device, the method comprising;

providing the compression therapy device comprising
        an inflatable compression sleeve comprising at least one compression cell and the inflatable compression sleeve adapted to deliver compressive force to relieve a medical condition;
        a source of fluid for inflating the compression sleeve, and
        a controller for controlling the inflation of the compression sleeve, wherein the controller comprises at least one sensor associated with the compression sleeve, at least one memory storage device to store a plurality of measurement data, at least one communication device, at least one user input interface device, and at least one user output interface device;
    before introducing the body part into the inflatable compression sleeve, evacuating, by the controller, the fluid from the at least one compression cell until at least one compression cell parameter measured by the at least one sensor attains at least one starting compression cell parameter value that is a standardized initial state of the at least one compression cell to obtain consistent measurement by the compression therapy device;
    after evacuating the fluid from the at least one compression cell, introducing the body part into the compression sleeve and verifying by the at least one sensor introduction of the body part into the compression sleeve after attaining the standardized initial state of the at least one compression cell measured by the at least one sensor;

after introducing the body part into the inflatable compression sleeve, inflating, by the controller, the at least one compression cell with the fluid until at least one controller parameter attains a first pre-set controller parameter value;

measuring, by the controller, at least one first compression cell parameter value; and calculating, by the controller, a volume of at least a portion of the patient body part based at least in part on the at least one first compression cell parameter value, wherein:

the at least one first pre-set controller parameter value is stored in the controller memory storage device, and calculating the volume of the body part comprises: providing, by the controller, a parameter value look-up table having a plurality of look-up values; and comparing, by the controller, the at least one first compression cell parameter value to one or more of the plurality of look-up values to determine the volume of the bodypart using the compression therapy device, wherein:

the at least one compression cell comprises a plurality of compression cells and each cell is configured with compression cell parameters independent from any other cell such that a starting compression cell parameter value for a first cell may be the same or different than a starting compression cell parameter of any other cell.

2. The method of claim 1, wherein the at least one sensor is in functional communication with the at least one compression cell.

3. The method of claim 1, wherein the at least one sensor comprises one or more of the following: a sensor of a pressure within the at least one compression cell, a sensor of a fluid flow rate into or out of the at least one compression cell, and a sensor of a deformation of a surface of the at least one compression cell.

4. The method of claim 1, wherein the at least one compression cell parameter comprises one or more of the following: a pressure within the at least one compression cell, a volume of the at least one compression cell, and a measurement of a deformation of a surface of the at least one compression cell.

5. The method of claim 1, wherein the inflatable compression sleeve comprises at least a first compression cell and a second compression cell.

6. The method of claim 5, wherein a first starting compression cell parameter value is associated with the first compression cell, and a second starting compression cell parameter value is associated with the second compression cell.

7. The method of claim 6, wherein the first starting compression cell parameter value differs from the second starting compression cell parameter value.

8. The method of claim 1, wherein the body part is a wrist, a lower arm, an upper arm, a shoulder, an abdomen, a groin, a hip, a buttock, a thigh, a lower leg, a calf, an ankle, or any combination thereof.

9. The method of claim 1, wherein the controller parameter comprises one or more of the following: an at least one compression cell inflation time, an at least one compression cell inflation rate, an at least one compression cell deflation time, an at least one compression cell deflation rate, an at least one compression cell evacuation time, an at least one compression cell evacuation rate, an at least one compression cell pressure, an at least one compression cell inflation volume, and an at least one compression cell surface deformation.

10. The method of claim 1, wherein the at least one first compression cell parameter value comprises one or more of the following: a pressure within the at least one compression cell, a volume of the at least one compression cell, and a measurement of a deformation of the at least one compression cell.

11. The method of claim 1, wherein the at least one starting compression cell parameter value is stored in the controller memory storage device.

12. The method of claim 1, wherein the at least one starting compression cell parameter value is transmitted to the controller via the at least one user input interface device.

13. The method of claim 1, wherein the at least one starting compression cell parameter value is transmitted to the controller via at least one communication device.

14. The method of claim 1, wherein the at least one first pre-set controller parameter value is transmitted to the controller via the at least one user input interface device.

15. The method of claim 1, wherein the at least one first pre-set controller parameter value is transmitted to the controller via at least one communication device.

16. The method of claim 1, further comprising interpolating the at least one first compression cell parameter value between any two of the plurality of look-up values.

17. The method of claim 1, further comprising: deflating the at least one compression cell until the at least one controller parameter attains a second pre-set controller parameter value; and measuring at least one second compression cell parameter value.

* * * * *